(12) United States Patent
Dolitzky

(10) Patent No.: US 6,992,191 B2
(45) Date of Patent: Jan. 31, 2006

(54) HYDROGENATION OF PRECURSORS TO THIAZOLIDINEDIONE ANTIHYPERGLYCEMICS

(75) Inventor: Ben-Zion Dolitzky, Petach Tiqva (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 10/324,928

(22) Filed: Dec. 20, 2002

(65) Prior Publication Data

US 2003/0153765 A1 Aug. 14, 2003

Related U.S. Application Data

(60) Provisional application No. 60/342,437, filed on Dec. 20, 2001.

(51) Int. Cl.
| | |
|---|---|
| C07D 417/10 | (2006.01) |
| C07D 277/34 | (2006.01) |
| A61K 31/4439 | (2006.01) |
| A61K 31/427 | (2006.01) |

(52) U.S. Cl. .................... 546/280.4; 514/342; 514/369; 546/280.4; 548/183

(58) Field of Classification Search ............. 546/280.4, 546/340; 514/342, 369, 225.2; 548/183
See application file for complete search history.

(56) References Cited

U.S. PATENT DOCUMENTS

| | | | | |
|---|---|---|---|---|
| 5,002,953 | A | | 3/1991 | Hindley |
| 5,710,152 | A | * | 1/1998 | Nagao et al. ............. 514/225.2 |
| 5,952,509 | A | * | 9/1999 | Saito et al. ................. 546/340 |
| 6,248,363 | B1 | * | 6/2001 | Patel et al. ................. 424/497 |

OTHER PUBLICATIONS

J. Cossy et al., "A Short Synthesis of Troglitazone: An Antidiabetic Drug for Treating Insulin Resistance," Bioorganic and Medicinal Chemistry Letters 9, pp. 3439–3440 (1990).

Shigeo Nishimura, *Handbook of Heterogeneous Catalytic Hydrogenation for Organic Synthesis*, Chapter 1, pp. 1–51 (2001).

\* cited by examiner

*Primary Examiner*—Kamal A. Saeed
(74) *Attorney, Agent, or Firm*—Kenyon & Kenyon

(57) ABSTRACT

Provided is a method of hydrogenating the exocyclic double bond of a thiazolidinedione precursor in a method of making a thiazolidinedione antihyperglycemic, for example pioglitazone, including work-up steps to afford pure thiazolidinedione antihyperglycemic.

45 Claims, No Drawings

HYDROGENATION OF PRECURSORS TO THIAZOLIDINEDIONE ANTIHYPERGLYCEMICS

RELATED APPLICATIONS

The present application claims the benefit of U.S. Provisional Patent Application No. 60/342,437, filed Dec. 20, 2001.

FIELD OF THE INVENTION

The present invention relates to a method of making thiazolidinedione antihyperglycemics that includes the step of catalytic hydrogenation of a penultimate thiazolidinedione precursor.

BACKGROUND OF THE INVENTION

Diabetes is a disorder of metabolism in which either the pancreas produces too little or no insulin, or the body cells do not respond to the insulin that is produced. In type I diabetes, the pancreas does not produce any insulin. In type II diabetes, also known as adult onset diabetes, there are two potential problems: the pancreas produces too little insulin, or the body cells do not respond to the insulin that is produced. In either scenario, the glucose cannot efficiently move from the blood to the cells, which leads to a buildup of glucose in the blood and an overflow into the urine. As a result, the body loses its main source of fuel. Administering insulin or oral antihyperglycemic agents allows the glucose to enter the cells more efficiently, thus providing a source of fuel.

Thiazolidinedione antihyperglycemics (benzylidenethiazolidinedione antihyperglycemics) are a class of drugs, useful in treating type II diabetes and other disorders relating to insulin resistance, that share a 5-(4-alkoxyphenyl)methyl-2,4-thiazolidinedione (I) pharmacophore.

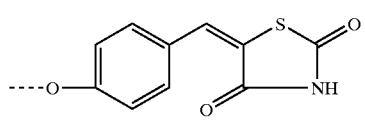

Pioglitazone is an oral thiazolidinedione antihyperglycemic agent that acts primarily by decreasing insulin resistance. Pharmacological studies indicate that pioglitazone improves sensitivity to insulin in muscle and adipose tissue and inhibits hepatic gluconeogenesis. Pioglitazone improves glucose resistance while reducing circulating insulin levels.

Pioglitazone, as its hydrochloride, is currently marketed as ACTOS®. Pioglitazone hydrochloride has the chemical name [(±)5-[[4-[2-(5-ethyl-2-pyridinyl)ethoxy]phenyl] methyl]-2,4-] thiazolidinedione monohydrochloride. (CAS Registry No 111025-46-8). The chemical structure of pioglitazone is shown as structure II.

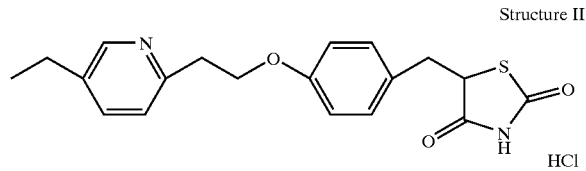

Structure II

U.S. Pat. No. 5,952,509, incorporated herein by reference, discloses methods for the synthesis of pioglitazone.

Rosiglitazone, 5-[4-[2-[N-methyl-N-(pyridin-2-yl) aminoethoxy]phenyl]methyl-2,4-thiazolidinedione, and troglitazone, 5-[4-[(6-hydroxy-2,5,7,8-tetramethylchroman-2-yl)methoxy]benzyl]-2,4-thiazolidinedione, are also a thiazolidinedione antihyperglycemics useful in treating type II diabetes and other disorders relating to insulin resistance. Rosiglitazone is marketed under the trade name Avandia®. Troglitazone has been marketed under the trade name Prelay®.

Methods for making pioglitazone, rosiglitazone, and troglitazone may proceed via a thiazolidinedione precursor having an exocyclic carbon-carbon double bond at the 5 position of a thiazolidinedione ring. The method of making pioglitazone disclosed in U.S. Pat. No. 5,952,509 is such a method. In such methods, the carbon-carbon double bond must be hydrogenated to a carbon-carbon single bond to form the thiazolidinedione antihyperglycemic. Catalytic hydrogenation over a supported catalyst, a method generally well known in the art, has been used to this end.

Synthesis of rosiglitazone via a thiazolidinedione precursor is disclosed in, for example, U.S. Pat. No. 5,002,953 (the '953 patent). Synthesis of troglitazone via a thiazolidinedione precursor is disclosed in J. Cossy et al., *A Short Synthesis of Troglitazone: An Antidiabetic Drug for Treating Insulin Resistance*, 9 Bioorganic and Medicinal Chemistry Letters, 3439–3440 (1999).

When the thiazolidinedione precursor is a solid, which is usually the case, a solvent must be used in the hydrogenation step. Hydrogenation of the thiazolidinedione pioglitazone precursors in solvents such as dioxane and particularly DMF has been reported. Large quantities (up to 20 volumes) of such solvents are required. When these solvents may be used, higher pressures (e.g. 50–100 atm) and a large amount of catalyst (ratio of weight of catalyst to weight of precursor of 1 to 3) are required. Even with such large amounts of catalyst, longer reaction times, e.g. ≧72 hr in some cases, are required to obtain only fair yields, e.g. 35–40%.

SUMMARY OF THE INVENTION

The present invention provides, i.a., a method for making thiazolidinedione antihyperglycemics from a thiazolidinedione precursor that includes the step of catalytically hydrogenating a thiazolidinedione precursor having an exocyclic double bond at the 5 position of the thiazolidine ring in a high capacity solvent.

In one aspect, the present invention relates to a method of hydrogenating a thiazolidinedione precursor, especially a thiazolidinedione precursor for pioglitazone, rosiglitazone, or troglitazone, including the steps of: providing a solution of the thiazolidinedione precursor in a high capacity solvent, especially formic acid, combining the solution with a supported metal hydrogenation catalyst, exposing the combination of solution and hydrogenation catalyst to hydrogen gas, and isolating hydrogenated precursor.

In another aspect, the present invention relates to a method of hydrogenating a penultimate thiazolidinedione precursor, especially a penultimate thiazolidinedione precursor of pioglitazone, rosiglitazone, or troglitazone including the steps of: providing a solution of the penultimate thiazolidinedione precursor in a high capacity solvent, especially formic acid, wherein the concentration of the solution is at least about 0.25 g/mL, especially at least about 0.5 g/mL; combining the solution with a supported metal hydrogenation catalyst, especially one in which the metal is selected from platinum, palladium, ruthenium, rhodium, osmium, and iridium; and exposing the combination of solution and hydrogenation catalyst to hydrogen gas, or without hydrogen gas.

In still another aspect, the present invention relates to a method of hydrogenating a penultimate thiazolidinedione precursor, especially a penultimate thiazolidinedione precursor for pioglitazone, rosiglitazone, or troglitazone including the steps of: providing a solution of the penultimate thiazolidinedione precursor in a high capacity solvent, especially formic acid, wherein the concentration of the solution is at least about 0.25 g/mL, especially at least about 0.5 g/mL; combining the solution with a supported metal hydrogenation catalyst selected from platinum, ruthenium, rhodium, osmium, iridium, and, especially, palladium, whereby the ratio of the weight of metal to the weight of precursor is about 0.03:1 or less, especially about 0.02:1; exposing the combination of solution and hydrogenation catalyst to hydrogen gas at a pressure between about 1 and about 10 Atm and a temperature between about 40° C. and about 100° C., and isolating the thiazolidinedione antihyperglycemic.

In still another aspect, the present invention provides a method for making pioglitazone including the step of catalytically hydrogenating 5-[4-[2-[5ethylpyridin-2-yl]ethoxy]phenyl]methenyl-2,4-thiazolidinedione in solution in a high capacity solvent, especially formic acid, using a supported metal catalyst wherein the metal is selected from platinum, ruthenium, rhodium, osmium, iridium, and, especially, palladium and the amount of catalyst is such that the ratio of the weight of the metal to the weight of precursor is less than about 0.03:1, especially 0.02:1 or less; exposing the combination of solution and hydrogenation catalyst to hydrogen gas at a pressure between about 1 and 10 Atm. and a temperature between about 40° C. and about 100° C., especially 75° to 85° C.; and isolating pioglitazone.

In still a further aspect, the present invention relates to a method of making pure pioglitazone including the step of catalytically hydrogenating 5-[4-[2-[5ethylpyridin-2-yl]ethoxy]phenyl]methenyl-2,4-thiazolidinedione in solution in a high capacity solvent, especially formic acid, using a supported metal catalyst wherein the metal is selected from platinum, ruthenium, rhodium, osmium, iridium, and, especially, palladium and the amount of catalyst is such that the ratio of the weight of the metal to the weight of precursor is less than about 0.03:1, especially 0.02:1 or less; exposing the combination of solution and hydrogenation catalyst to hydrogen gas at a pressure between about 1 and 10 Atm. and a temperature between about 40° C. and about 100° C.; isolating the product of the catalytic hydrogenation and slurrying the isolated product in a slurry solvent selected from acetone, methanol, ethanol and isopropanol; and isolating pure pioglitazone.

In still a further aspect, the present invention relates to a method of making rosiglitazone including the step of catalytically hydrogenating 5-[4-[2-[N-methyl-N-(pyridin-2-yl)aminoethoxy]phenyl]methenyl-2,4-thiazolidinedione in solution in a high capacity solvent, especially formic acid, using a supported metal catalyst wherein the metal is selected from platinum, ruthenium, rhodium, osmium, iridium, and, especially, palladium and the amount of catalyst is such that the ratio of the weight of the metal to the weight of precursor is less than about 0.03:1, especially 0.02:1 or less; exposing the combination of solution and hydrogenation catalyst to hydrogen gas at a pressure between about 1 and 10 Atm and a temperature between about 40° C. and about 100° C.; and isolating rosiglitazone.

In still a further aspect, the present invention relates to a method of making pure rosiglitazone including the step of catalytically hydrogenating 5-[4-[2-[N-methyl-N-(pyridin-2-yl)aminoethoxy]phenyl]methenyl-2,4-thiazolidinedione in solution in a high capacity solvent, especially formic acid, using a supported metal catalyst wherein the metal is selected from platinum, ruthenium, rhodium, osmium, iridium, and, especially, palladium and the amount of catalyst is such that the ratio of the weight of the metal to the weight of precursor is less than about 0.03:1, especially 0.02:1 or less; exposing the combination of solution and hydrogenation catalyst to hydrogen gas at a pressure between about 1 and 10 Atm and a temperature between about 40° C. and about 100° C.; isolating the product of the catalytic hydrogenation and slurrying the isolated product in a slurry solvent selected from acetone, methanol, ethanol and isopropanol; and isolating pure rosiglitazone.

In still a further aspect, the present invention relates to a method of making troglitazone including the step of catalytically hydrogenating 5-[4-[(6-hydroxy-2,5,7,8-tetramethylchroman-2-yl)methoxy]phenyl]methenyl-2,4-thiazolidinedione in solution in a high capacity solvent, especially formic acid, using a supported metal catalyst wherein the metal is selected from platinum, ruthenium, rhodium, osmium, iridium, and, especially, palladium and the amount of catalyst is such that the ratio of the weight of the metal to the weight of precursor is less than about 0.03:1, especially 0.02:1 or less; exposing the combination of solution and hydrogenation catalyst to hydrogen gas at a pressure between about 1 and 10 Atm and a temperature between about 40° C. and about 100° C.; and isolating troglitazone.

In still a further aspect, the present invention relates to a method of making pure troglitazone including the step of catalytically hydrogenating 5-[4-[(6-hydroxy-2,5,7,8-tetramethylchroman-2-yl)methoxy]phenyl]methenyl-2,4-thiazolidinedione in solution in a high capacity solvent, especially formic acid, using a supported metal catalyst wherein the metal is selected from platinum, ruthenium, rhodium, osmium, iridium, and, especially, palladium and the amount of catalyst is such that the ratio of the weight of the metal to the weight of precursor is less than about 0.03:1, especially 0.02:1 or less; exposing the combination of solution and hydrogenation catalyst to hydrogen gas at a pressure between about 1 to 10 Atm. and a temperature between about 40° C. and about 100° C.; isolating the product of the catalytic hydrogenation and slurrying the isolated product in a slurry solvent selected from acetone, methanol, ethanol and isopropanol; and isolating pure rosiglitazone.

DETAILED DESCRIPTION OF THE INVENTION

The present invention provides a method for making a thiazolidinedione antihyperglycemic via a thiazolidinedione precursor having an exocyclic double bond at the 5 position of the thiazolidinedione ring thereof, which method includes the step of catalytic hydrogenation with a supported metal catalyst in which less catalyst is required (as little as 0.2 gram of catalyst per gram of precursor) and in which good yields (e.g. ≧85%) can be realized in reaction times of 30 hr or less.

The present invention provides a method for making pioglitazone, rosiglitazone, and troglitazone from respective thiazolidinedione precursors that includes the step of catalytically hydrogenating the thiazolidinedione precursor having an exocyclic carbon-carbon double bond at the 5 position of the thiazolidine ring, wherein the hydrogenation is carried-out in a high capacity solvent.

A thiazolidinedione precursor is a compound that is an intermediate in a process for making a thiazolidinedione antihyperglycemic, such as the process disclosed in U.S. Pat. No. 5,952,509 incorporated herein by reference, and that has a thiazolidinedione moiety. Thiazolidinedione pioglitazone precursors useful in the practice of the present invention have an exocyclic double bond at the 5 position of the thiazolidinedione moiety as illustrated below.

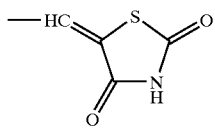

Preferred thiazolidinedione pioglitazone precursors are penultimate thiazolidinedione precursors. A penultimate thiazolidinedione precursor differs structurally from the thiazolidinedione antihyperglycemic itself in that the penultimate thiazolidinedione precursor has an exocyclic double bond at the 5-position of the thiazolidinedione moiety. A penultimate thiazolidinedione precursor may also have protected functional groups groups (i.e. protected hydroxyl groups). Hydrogenation of this exocyclic double bond, and removal of protecting groups if any, yields the thiazolidinedione antihyperglycemic, which is isolated from the reaction mixture. The compound 5-[4-[2-[5-ethylpyridin-2-yl]ethoxy]phenyl]methenyltiazolidine-2,4-dione (hereafter "PIE") is an example of a penultimate thiazolidinedione precursor for pioglitazone.

Thus, hydrogenation of the exocyclic double bond of the penultimate thiazolidinedione pioglitazone precursor PIE affords pioglitazone as illustrated in reaction I below in which the supported metal hydrogenation catalyst is palladium-on-carbon (Pd/C) catalyst.

Reaction I

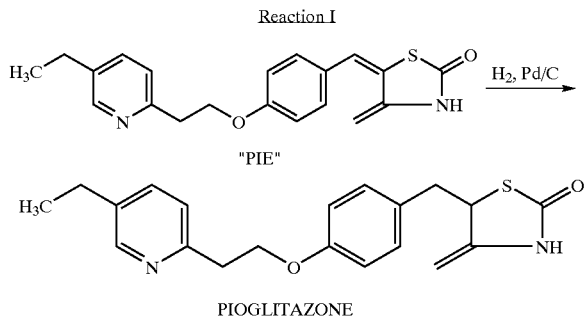

Synthesis of PIE is taught, for example, in U.S. Pat. No. 5,952,509.

Hydrogenation of the penultimate thiazolidinedione precursor 5-[4-[2-[N-methyl-N-(pyridin-2-yl)aminoethoxy]phenyl]methenyl-2,4-thiazolidinedione affords rosiglitazone. Synthesis of 5-[4-[2-[N-methyl-N-(pyridin-2-yl)aminoethoxy]phenyl]methenyl-2,4-thiazolidinedione is disclosed in, for example, the '953 patent. Likewise, hydrogenation of the penultimate thiazolidinedione precursor 5-[4-[(6-hydroxy-2,5,7,8-tetramethylchroman-2-yl)methoxy]phenyl]methenyl-2,4-thiazolidinedione, or hydroxy group protected derivatives thereof, affords troglitazone. See J. Cossy et al., supra.

The hydrogenation step of the present invention is catalytic hydrogenation over a supported metal hydrogenation catalyst. Supported metal hydrogenation catalysts are well known in the art and have a metal deposited, absorbed, or coated on or in a solid support. Examples of metals that can be used include platinum, palladium, ruthenium, rhodium, osmium, and iridium. Many solid supports are known in the art. Particulate carbon is a well-known useful solid support. Supported metal hydrogenation catalysts are described in, for example, Shigeo Nishimura, *Handbook of Heterogeneous Catalytic Hydrogenation for Organic Synthesis,* Chpt. 1, (2001). Palladium catalyst supported on carbon (Pd/C catalyst) is a preferred supported metal hydrogenation catalyst for use in the present invention. An example of a preferred Pd/C catalyst useful in the practice of the present invention is 87L powder catalyst (10% Pd by weight) available from Johnson Matthey, West Depford, N.J.

In the practice of the present invention, the catalytic hydrogenation of the exocyclic double bond of the thiazolidinedione precursor is carried-out in a high-capacity solvent. A high capacity solvent is one in which one gram (1 g) of thiazolidinedione pioglitazone precursor dissolves in about 5 milliliters (5 mL) or less of solvent. Preferred high capacity solvents are those in which 1 g of precursor dissolves in 4 mL or less of solvent at a temperature between about 25° C. and about 45° C. Formic acid is particularly preferred high capacity solvent in the practice of the present invention. When used as the high capacity solvent, the formic acid can have up to about 15% by weight water.

In the practice of the present invention, the weight of supported metal hydrogenation catalyst used is preferably such that the ratio of the weight of metal to the weight of precursor to be hydrogenated is about 0.05:1 or less, preferably 0.03:1 or less. Most preferably, the amount of catalyst is such that the ratio of the weight of metal to the weight of precursor is about 0.02:1 or less. The weight of the metal is calculated by multiplying the weight of the supported metal catalyst by the percent catalyst loading expressed as a decimal. Thus, if the weight ratio of 10% loaded supported metal catalyst to precursor is 0.2:1; the ration of the weight of metal to the weight of precursor is 0.02:1.

The catalytic hydrogenation of thiazolidinedione pioglitazone precursor is carried-out in conventional equipment well known in the art. For example, in an autoclave. The autoclave can be equipped with a stirrer or it can be of the shaker-type. The hydrogen pressure to which the solution is exposed during hydrogenation is not critical to realizing the benefits of the present invention. In particular embodiments, hydrogen gas is not used. Typically, the solution is exposed to a hydrogen pressure between about 1 and about 10 Atm, preferably about 2 to about 5 Atm.

In a particular embodiment in which formic acid is the high capacity solvent, hydrogenation is effected without exposing the solution of thiazolidinedione precursor, preferably penultimate precursor, to hydrogen gas. In this embodiment, a solution of the thiazolidinedione precursor in formic acid is combined with supported metal hydrogenation catalyst and heated at about 40° C. to about 100° C. The amounts of solvent and catalyst are the same as in other embodiments.

In a preferred embodiment, the hydrogenation reactor (e.g. autoclave) is purged at least once, preferably at regular intervals (e.g. 30 min.), during the hydrogenation reaction. In a purging step, gas supply to the reactor is closed off, the reactor is vented to the atmosphere, and gas supply is re-established to repressurize the reactor with hydrogen gas.

The skilled artisan will recognize that any operation or procedure that allows for refreshment of the atmosphere in the reactor is a purging step and such operations that allow refreshment of the atmosphere in the reactor are within the scope of the invention.

The temperature at which the catalytic hydrogenation in a high capacity solvent of the present invention is carried-out is not critical and will be influenced by, among other things, practical considerations such as reactor throughput and operational safety. Typically, the temperature will be between about 40° C. and 100° C., preferably between about 70° C. and about 90° C., but temperatures $\geq$100° C. can be used without sacrificing the benefits of the present invention.

The time of hydrogenation is not critical. However, it is an advantage of the present invention over prior art methods that, parameters such as $H_2$ pressure, catalyst dosage (g catalyst per g precursor), catalyst loading (percent of catalyst not consisting of carbon or other support), and catalyst surface area (such as can be measured by, for example, nitrogen absorption) being equal, the present invention allows for shorter hydrogenation times (time to completion of reaction), without sacrifice in conversion, yield, or purity. Compared to results obtained practicing methods of the prior art, higher degrees of reaction completion and higher yields of pioglitazone are obtained in less hydrogenation time when the method of the present invention is used. The skilled artisan will know to judge completion of the reaction by, for example, noting a cessation of hydrogen uptake, or by sampling the contents of the reactor using known techniques and analyzing the sample using, for example, gas chromatography.

In the practice of preferred embodiments of the catalytic hydrogenation in a high capacity solvent, a slurry is obtained wherein the hydrogenation product is in solution in the high capacity solvent at the completion of hydrogenation. The product can be recovered by, for example, adding a non-solvent to the solution or by concentrating the solution, especially under vacuum, whereby a suspension or slurry forms from which the product can be isolated. In this and other embodiments of the present invention, isolation can be by any means known in the art, for example filtration (gravity or suction) or centrifugation, to mention just two.

The conversions realized in the method of the present invention are at least about 99% and the hydrogenation product may contain less than 0.25% residual thiazolidinedione precursor.

In a further embodiment, the present invention provides a recovery process for work-up of the thiazolidinedione antihyperglycemic product of hydrogenation of a penultimate thiazolidinedione precursor to afford pure thiazolidinedione antihyperglycemic. The recovery process includes the steps of separating catalyst from the solution at the completion of the hydrogenation, adding a crystallization solvent to the solution from which catalyst was separated, cooling the combination whereby a solid precipitate of thiazolidinedione antihyperglycemic forms, and isolating the thiazolidinedione antihyperglycemic.

In preferred embodiments, the solution from which catalyst has been separated is concentrated before being combined with crystallization solvent. Any degree of concentration can improve recovery. Typically, the solution will be concentrated to about 60% to about 40% of its initial weight.

Acetone and lower alkyl alcohols can be used as crystallization solvents. Lower alkyl alcohols useful in the practice of the present invention have the formula ROH, wherein R is a linear or branched alkyl group having 6 carbon atoms. Methanol, ethanol, and isopropanol are preferred lower alkyl alcohols. The skilled artisan will know to adjust the amount of crystallization solvent according to, for example, the concentration of the solution with which the crystallization solvent is combined. If the solution is not concentrated, the amount of crystallization solvent will typically be about 7 to about 12 timed the volume of solution.

The thiazolidinedione antihyperglycemic isolated from the recovery process is pure thiazolidinedione antihyperglycemic. Pure denotes that the antihyperglycemic has a purity of at least about 99.7%, expressed as area percent, as determined by high-pressure liquid chromatography (HPLC) according to the method described below.

Purity (area-% purity) is determined by HPLC using a 250×4.6 mm column packed with YMC ODS AQ (5$\mu$) at 40° C. and eluent flow rate of 1.0 ml/min. Detection is with a UV detector operating at 220 nm. Elution is by linear gradient elution according to the following program:

| Elution Time (min) | % Eluent A | % Eluent B |
|---|---|---|
| 0 | 100 | 0 |
| 3 | 100 | 0 |
| 33 | 20 | 80; | wherein eluent A is 60% 0.01M aqueous trifluoroacetic acid (adjusted to pH 2.5 with 1N $KOH_{aq}$) and 40% methanol and wherein eluent B is 30% 0.01M aqueous trifluoroacetic acid (adjusted to pH 2.5 with 1N $KOH_{aq}$). The nominal injection volume is 20 $\mu$L.

The present invention is further illustrated by the following non-limiting Examples 1 to 4. Examples 5 and 6 are comparative examples showing the results obtained when following a method from the prior art that does not use a high capacity solvent.

EXAMPLE 1

One gram of PIE is charged to a test tube. One milliliter of formic acid is added to the test tube. The test tube is agitated by hand in a bath maintained at 45° C. A clear solution forms, showing that formic acid is a high capacity solvent.

EXAMPLE 2

Ten grams of Pd/C catalyst (Johnson Matthey 87L, 10% Pd), 200 ml formic acid, and 50 g PIE were charged to a laboratory autoclave. The autoclave was closed, charged with $H_2$, and heated to 60° C. The $H_2$ pressure was adjusted to 2 Atm. The contents of the autoclave were maintained at 60 C under 2 Atm $H_2$ pressure for 30 hours.

Heating was stopped, the pressure released, and the autoclave opened while the contents, a slurry, were still warm. The slurry was filtered warm and washed with two 20 ml aliquots of formic acid. Analysis showed that $\geq$99% of PIE had been converted to pioglitazone; only 0.24% of the starting PIE remained unreacted.

One and eight-tenths liter of acetone were added to the recovered solution and the resulting solution was allowed to stand for 5 hrs, during which time the product crystallized from solution. The slurry was filtered and washed with 20 ml of a 9:1 mixture of acetone and formic acid. The recovered product was dried to give 42 g (yield 84%) pioglitazone having a purity of $\geq$99.7% (HPLC).

EXAMPLE 3

Ten grams of Pd/C catalyst (Johnson Matthey 87L, 10% Pd), 200 ml formic acid, and 50 g PIE were charged to a laboratory autoclave. The autoclave was closed, charged with $H_2$, and heated to 60° C. The $H_2$ pressure was adjusted to 6 Atm. The contents of the autoclave were maintained at 60 C under 6 Atm $H_2$ pressure for 30 hours.

Heating was stopped, the pressure released, and the autoclave opened while the contents, a slurry, were still warm. The slurry was filtered warm and washed with two 20 ml aliquots of formic acid. Analysis showed that ≧99% of PIE had been converted to pioglitazone; only 0.24% of the starting PIE remained unreacted.

One and eight-tenths liter of acetone were added to the recovered solution and the resulting solution was allowed to stand for 5 hrs, during which time the product crystallized from solution. The slurry was filtered and washed with 20 ml of a 9:1 mixture of acetone and formic acid. The recovered product was dried to give 42 g (yield 84%) pioglitazone having a purity of ≧99.7% (HPLC).

EXAMPLE 4

PIE (50 kg.) was dissolved in formic acid (500 kg,). Supported metal catalyst (40 kg. of 10% Pd on carbon, KF=50%) was added and the suspension was heated to 80° C. and pressureized to 2 Atm with hydrogen. The reactor was purged at 30 minute intervals throughout the hydrogenation.

After 20 hours, the suspension was cooled to room temperature and the catalyst separated by filtration. The solution was concentrated to 80 kg. Ethanol (632 kg) was added to the solution at 75° C. and the resulting mixture was gradually cooled to <13° C. The precipitate formed was isolated by filtration and washed with ethanol. Yield: 30 kg after drying.

EXAMPLE 5

One gram of PIE and 1 ml or dimethyl formamide (DMF) are charged to a test tube. The test tube is agitated by hand in a bath maintained at 45° C. All of the PIE does not dissolve. Three 1 ml aliquots of DMF are added to the test tube (total 4 ml). All of the PIE does not dissolve showing that DMF is not a high capacity solvent.

EXAMPLE 4

Fifty grams of PIE, 250 ml of DMF, and 50 g Pd/C catalyst (Johnson Matthey 87L) were charged to a laboratory autoclave. The autoclave was closed, charged with $H_2$, and heated to 50° C. The $H_2$ pressure was adjusted to 3 atm. The contents of the autoclave were maintained at 500 C under 3 atm $H_2$ for 72 hours.

Heating was ceased, the pressure released and the product worked-up by a procedure analogous to that used in Example 2. Analysis showed that ~68.5% of PIE had been converted to pioglitazone containing about 3.5% impurities (HPLC). About 26.5% of the PIE remained unreacted.

What is claimed is:

1. A method of catalytically hydrogenating the exocyclic double bond of a penultimate thiazolidinedione precursor comprising the steps of:
   a) providing a solution of the penultimate thiazolidinedione precursor in a high capacity solvent, which is formic acid,
   b) combining the solution with a supported metal hydrogenation catalyst in a reactor, and
   c) exposing the combination of solution and hydrogenation catalyst to hydrogen gas.

2. The method of claim 1 wherein the concentration of the solution is at least about 0.25 g/mL.

3. The method of claim 2 wherein the concentration of the solution is at least about 0.5 g/mL.

4. The method of claim 1 wherein the supported metal hydrogenation catalyst comprises a metal selected form the group consisting of platinum, palladium, ruthenium, rhodium, osmium, and iridium.

5. The method of claim 4 wherein the amount of supported metal hydrogenation catalyst used is such that the ratio of the weight of the metal to the weight of precursor is less than about 0.05:1.

6. The method of claim 5 wherein the supported metal hydrogenation catalyst comprises palladium.

7. The method of claim 6 wherein the supported hydrogenation metal catalyst is palladium (10%) supported on charcoal and the amount of supported catalyst used is such that the ratio of the weight of palladium to the weight of precursor is about 0.02:1.

8. The method of claim 1 further comprising the step of purging the reactor in which the hydrogenation is conducted at least once prior to the end of the hydrogenation.

9. The method of claim 1 wherein the penultimate thiazolidinedione precursor is 5-[4-[2-[5ethylpyridin-2-yl]ethoxy]phenyl]methenyl-2,4-thiazolidinedione.

10. The method of claim 1 wherein the penultimate thiazolidinedione precursor is 5-[4-[(6-hydroxy-2,5,7,8-tetramethylchroman-2-yl)methoxy]phenyl]methenyl-2,4-thiazolidinedione.

11. The method of claim 1 wherein the penultimate thiazolidinedione precursor is 5-[4-[2-[N-methyl-N-(pyridin-2-yl)aminoethoxy]phenyl]methenyl-2,4-thiazolidinedione.

12. A method of catalytically hydrogenating the exocyclic double bond of a penultimate thiazolidinedione precursor comprising the steps of:
   a) providing a solution of the penultimate thiazolidinedione precursor in formic acid solvent,
   b) combining the solution with a supported metal hydrogenation catalyst in a reactor, wherein the supported metal hydrogenation catalyst comprises a metal selected from the group consisting of platinum, palladium, ruthenium, rhodium, osmium, and iridium, and
   c) heating the combination to a temperature of about 40° C. to about 100° C.

13. The method of claim 12 wherein the metal is palladium.

14. The method of claim 13 wherein the supported metal hydrogenation catalyst is palladium on carbon and the amount of catalyst is such that the ration of the weight of palladium to the weight of penultimate thiazolidinedione precursor is about 0.05:1 or less.

15. The method of claim 12 wherein the combination of solution and supported metal hydrogenation catalyst is exposed to hydrogen gas.

16. The method of claim 15 wherein the reactor in which the hydrogenation is conducted is purged at least once prior to the end of the hydrogenation.

17. A method of making a thiazolidinedione antihyperglycemic comprising the step of catalytically hydrogenating a penultimate thiazolidinedione precursor in solution in a high capacity solvent using a supported metal hydrogenation catalyst comprising a metal selected from platinum, palladium, ruthenium, rhodium, osmium, and iridium, wherein essentially all of the product of hydrogenation is in solution in the high capacity solvent when hydrogenation is completed.

18. The method of claim 17 wherein the high capacity solvent consists essentially of formic acid.

19. The method of claim 17 wherein the solution has a concentration of at least about 0.25 g/mL.

20. The method of claim 17 wherein the amount of catalyst used is such that the ratio of the weight of metal to the weight of penultimate thiazolidinedione precursor is less than about 0.05:1.

21. The method of claim 20 wherein the amount of catalyst used is such that the ratio of the weight of metal to the weight of penultimate thiazolidinedione precursor is about 0.03:1 or less.

22. The method of claim 21 wherein the amount of catalyst is such that the ratio of the weight of metal to the weight of penultimate thiazolidinedione precursor is about 0.02:1 or less.

23. The method of claim 22 wherein the metal is platinum and the high capacity solvent consists essentially of formic acid.

24. The method of claim 17 wherein the catalytic hydrogenation is carried-out at a temperature of about 40° C. to about 100° C.

25. The method of claim 17 further comprising the steps of:
   separating supported metal catalyst from the solution,
   combining the solution from which catalyst has been separated with a crystallization solvent that is acetone, or a lower aliphatic alcohol,
   cooling the combination, and
   isolating the solid thiazolidinedione antihyperglycemic formed.

26. The method of claim 25 wherein the cooling is to a temperature of about 15° C. or less.

27. The method of claim 25 further comprising the step of concentrating the solution from which catalyst was separated prior to combining the solution with the crystallization solvent.

28. The method of claim 25 wherein the lower aliphatic alcohol is selected from the group consisting of methanol, ethanol, and isopropanol.

29. The method of claim 25 wherein the thiazolidinedione antihyperglycemic is pioglitazone.

30. The method of claim 25 wherein the thiazolidinedione antihyperglycemic is troglitazone.

31. The method of claim 25 wherein the thiazolidinedione antihyperglycernic is rosiglitazone.

32. A method of making a pure thiazolidinedione antihyperglycemic comprising the steps of:
   a) catalytically hydrogenating a penultimate thiazolidinedione precursor in solution in a high capacity solvent using a supported metal hydrogenation catalyst comprising a metal selected from platinum, palladium, ruthenium, rhodium, osmium, and iridium, wherein essentially all of the product of hydrogenation is in solution in the high capacity solvent when hydrogenation is completed,
   b) separating the supported metal catalyst from the solution,
   c) combining the solution from which catalyst has been separated with a crystallization solvent that is acetone or a lower aliphatic alcohol,
   d) cooling the combination, and
   e) isolating the solid pure thiazolidionedione antihyperglycemic formed.

33. The method of claim 32 wherein the high capacity solvent is formic acid.

34. The method of claim 32 wherein the lower aliphatic alcohol is selected front methanol, ethanol, and isopropanol.

35. The method of claim 32 wherein the cooling is to a temperature of about 15° C. or less.

36. The method of claim 32 wherein the thiazolidiendione antihyperglycemic is pioglitazone.

37. The method of claim 32 wherein the thiazolidiendione antihyperglycemic is rosiglitazone.

38. The method of claim 32 wherein the thiazolidinedione antihyperglyccmic is troglitazone.

39. In a method of making pioglitazone, the step of catalytically hydrogenating 5-[4-[2-[5ethylpyridin-2-yl]ethoxy]phenyl]methenyl-2,4-thiazolidinedione in formic acid solution using a palladium-on-charcoal supported hydrogenation catalyst wherein the concentration of the solution is at least about 0.2 g/mL and wherein the amount of supported catalyst used is such that the ratio of the weight of palladium metal to weight of 5-[4-[2-[5ethylpyridin-2-yl]ethoxy]phenyl]methenyl-2,4-thiazolidinedione about 0.02:1 or less.

40. In a method of making rosiglitazone, the step of catalytically hydrogenating 5-[4-[2-[N-methyl-N-(pyidin-2-yl)aminoethoxy]phenyl]methenyl-2,4-thiazolidinedione in formic acid solution using a palladium-on-charcoal supported hydrogenation catalyst wherein the concentration of the solution is at least about 0.2 g/mL and wherein the amount of supported catalyst used is such that the ratio of the weight of palladium metal to weight of 5-[4-[2-[5ethylpyridin-2-yl]ethoxy]phenyl]methenyl-2,4-thiazolidinedione is about 0.02:1 or less.

41. In a method of making troglitazone, the step of catalytically hydrogenating 5-[4-[(6-hydroxy-2,5,7,8-tetramethylchroman-2-yl)methoxy]phenyl]methenyl-2,4-thiazolidinedione in formic acid solution using a palladium-on-charcoal supported hydrogenation catalyst wherein the concentration of the solution is at least about 0.2 g/mL and wherein the amount of supported catalyst used is such that the ratio of the weight of palladium metal to weight of 5-[4-[2-[5ethylpyridin-2-yl]ethoxy]phenyl]methenyl-2,4-thiazolidinedione is about 0.02:1 or less.

42. The method of claim 1 wherein the solution and hydrogenation catalyst are exposed at a pressure of about 1 to about 10 atmospheres.

43. The method of claim 39 wherein the pressure is about 2 to about 5 atmospeheres.

44. The method of claim 12 heating is at a pressure of about 1 to about 10 atmospheres.

45. The method of claim 44 wherein the pressure is about 2 to about 5 atmospheres.

* * * * *